(12) United States Patent
Fleming et al.

(10) Patent No.: US 6,908,453 B2
(45) Date of Patent: Jun. 21, 2005

(54) MICRONEEDLE DEVICES AND METHODS OF MANUFACTURE

(75) Inventors: Patrick R. Fleming, Lake Elmo, MN (US); Michael D. Delmore, Grant, MN (US); Luther E. Erickson, Grant, MN (US); Richard H. Ferber, Fridley, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 106 days.

(21) Appl. No.: 10/051,745

(22) Filed: Jan. 15, 2002

(65) Prior Publication Data

US 2003/0135161 A1 Jul. 17, 2003

(51) Int. Cl.[7] .................................. A61M 5/00
(52) U.S. Cl. ........................ 604/173; 604/272
(58) Field of Search ................ 604/93.01, 173, 604/264, 272; 606/167, 172, 181, 183, 184–185

(56) References Cited

U.S. PATENT DOCUMENTS

| | | | |
|---|---|---|---|
| 3,964,482 A | | 6/1976 | Gerstel et al. |
| 4,109,655 A | * | 8/1978 | Chacornac .................. 604/47 |
| 5,620,095 A | | 4/1997 | Delmore et al. |
| 6,099,682 A | | 8/2000 | Krampe et al. |
| 6,558,361 B1 | * | 5/2003 | Yeshurun .................. 604/272 |
| 6,663,820 B2 | * | 12/2003 | Arias et al. ................ 264/496 |
| 2003/0199812 A1 | * | 10/2003 | Rosenberg .................. 604/47 |

FOREIGN PATENT DOCUMENTS

| | | |
|---|---|---|
| EP | 1 086 718 A1 | 3/2001 |
| EP | 1 086 719 A1 | 3/2001 |
| EP | 1 088 642 A1 | 4/2001 |
| GB | 2 221 394 A | 2/1990 |
| WO | WO 94/25259 A1 | 11/1994 |
| WO | WO 96/33839 A1 | 10/1996 |
| WO | WO 97/03718 A1 | 2/1997 |
| WO | WO 98/00193 | 1/1998 |
| WO | WO 98/28037 | 7/1998 |
| WO | WO 99/64580 A1 | 12/1999 |
| WO | WO 00/05166 A1 | 2/2000 |
| WO | WO 00/74763 A3 | 12/2000 |
| WO | WO 00/74763 A2 | 12/2000 |
| WO | WO 00/74764 A1 | 12/2000 |
| WO | WO 01/36037 | 5/2001 |
| WO | WO 01/66065 | 9/2001 |
| WO | WO 01/93930 | 12/2001 |

* cited by examiner

*Primary Examiner*—LoAn H. Thanh
(74) *Attorney, Agent, or Firm*—Cheree Haswell Johnson

(57) ABSTRACT

Microneedle devices and methods of manufacturing the microneedle devices. The microneedle devices include microneedles protruding from a substrate, with the microneedles piercing a cover placed over the substrate surface from which the microneedles protrude. The cover and the microneedle substrate together define a capillary volume in fluid communication with the base of each microneedle. One manner of using microneedle arrays of the present invention is in methods involving the penetration of skin to deliver medicaments or other substances and/or extract blood or tissue. Manufacturing methods may include simultaneous application of pressure and ultrasonic energy when piercing the cover with the microneedles.

6 Claims, 7 Drawing Sheets

MICRONEEDLE DEVICES AND METHODS OF MANUFACTURE

The present invention relates to the field of microneedle devices and methods of manufacturing the same.

BACKGROUND

Arrays of relatively small structures, sometimes referred to as microneedles or micro-pins, have been disclosed for use in connection with the delivery and/or removal of therapeutic agents and other substances through the skin and other surfaces.

The vast majority of known microneedle devices include structures having a capillary or passageway formed through the needle. Because the needles are themselves small, the passageways formed in the needles must be limited in size. As a result, the passageways can be difficult to manufacture because of their small size and the need for accurate location of the passageways within the needles. Another potential problem of passageways small enough to fit within the microneedles is that the passageways may become easily obstructed or clogged during use.

As a result, a need existed for microneedle devices that include fluid passageways that are easier to manufacture and that are resistant to obstruction or clogging during use. This need was answered in part by copending and commonly assigned U.S. patent application Ser. No. 09/947,195, filed on Sep. 5, 2001 and entitled MICRONEEDLE ARRAYS AND METHODS OF MANUFACTURING THE SAME. The microneedles disclosed in that application include channels formed in their outer surfaces, with the channels extending from the base towards the tip of each microneedle. The channels provide convenient fluid paths in connection with the microneedles. The microneedle arrays disclosed in that application may also include conduit structures formed on the substrate surface to enhance fluid flow across the surface of the substrate from which the microneedles project. Once the microneedles have penetrated the skin, a sample of body fluid may flow through the channels to be collected by the conduit structure towards, for example, some type of sensor. Although the conduit structures can facilitate fluid transport in connection with the microneedles, improvements may still be possible with regard to transporting fluid quickly and efficiently across the devices to, e.g., sensors, etc.

SUMMARY OF THE INVENTION

The present invention provides microneedle devices and methods of manufacturing the microneedle devices. The microneedle devices include microneedles protruding from a substrate, with the microneedles piercing a cover placed over the substrate surface from which the microneedles protrude. The cover and the microneedle substrate together define a capillary volume in fluid communication with the base of each microneedle.

The capillary volume enhances the movement of fluid towards or away from the microneedles by wicking fluids towards or away from the microneedles. The wicking action may be accomplished by selection of suitable spacing between the substrate and the cover and/or by the selection of materials used for the various components in the devices. In some instances, coatings may be provided within the capillary volume, e.g., hydrophilic coatings, that may enhance the capillary wicking action within the capillary volume.

The capillary volume in the microneedle devices may be provided by simply spacing the cover from the substrate surface, or by including some standoff structure between the cover and the surface of the microneedle substrate that can define a minimum distance between the cover and the substrate. The standoff structure may be formed as a part of the substrate surface, a part of the cover, a part of both the substrate surface and the cover, or by a separate article or articles (e.g., loose fillers) interposed between the substrate and the cover.

The capillary volume may (in some embodiments) be defined, at least in part, by conduit structures formed on the surface of the substrate on which the microneedle array is located. The conduit structure may be provided in the form of depressions or grooves in the substrate surface. Alternatively, the conduit structures may be formed by barriers, similar to dikes, that protrude above the substrate surface.

The microneedle devices of the present invention may, in some embodiments include one or more sensor elements in fluid communication with the capillary volume, such that fluids traveling through the capillary volume contact the sensor element. The sensor element may be used to sense any of a number of properties and/or compositions in the fluids passing through the capillary volume. In one example, the sensor element can be a glucose test element. If, for example, the glucose test element includes glucose oxidaze, the fluid sample passing through the capillary volume may be assessed using electrochemical techniques. In some constructions, the cover, the substrate, or another element (e.g., a backing) may be provided with an electrically conductive circuit pattern to facilitate electrochemical analysis of the fluid sample. Alternatively, the sensor element may undergo an optical change dependent on the properties and/or composition of the fluid passing through the capillary volume. Other alternative sensing techniques will be known to those of skill in the art.

In one aspect, the present invention provides a microneedle device including a substrate having a first major surface; at least one microneedle projecting from the first major surface of the substrate, the at least one microneedle having a base proximate the first major surface of the substrate and a tip distal from the base; a cover with a first side facing the first major surface of the substrate and a second side facing away from the substrate, wherein the at least one microneedle penetrates through the first side and the second side of the cover; and a capillary volume located between the first major surface of the substrate and the first side of the cover; wherein the capillary volume contacts at least a portion of the base of the at least one microneedle.

In another aspect, the present invention provides a microneedle device including a substrate with a first major surface and a second major surface; at least one microneedle projecting from the first major surface of the substrate, the at least one microneedle including a base proximate the first major surface of the substrate and a tip distal from the base; a cover with a first side facing the first major surface of the substrate and a second side facing away from the substrate, wherein the at least one microneedle penetrates through the first side and the second side of the cover; a capillary volume located between the first major surface of the substrate and the first side of the cover; wherein the capillary volume contacts at least a portion of the base of the at least one microneedle; a backing proximate the second major surface of the substrate, wherein the backing extends past a periphery of the substrate; and a cap attached to the backing around the periphery of the substrate, wherein the first major surface of the substrate faces the cap, and wherein the substrate and the at least one microneedle are enclosed between the backing and the cap.

In another aspect, the present invention provides a method of manufacturing a microneedle device by providing a substrate having a first major surface and at least one microneedle projecting from the first major surface of the substrate, the at least one microneedle including a base proximate the first major surface of the substrate and a tip distal from the base; providing a cover having a first side facing the first major surface of the substrate; forcing the tip of the at least one microneedle through the cover; and forming a capillary volume located between the first major surface of the substrate and the first side of the cover; wherein the capillary volume contacts at least a portion of the base of the at least one microneedle.

These and other features and advantages of the invention may be described below in connection with various illustrative embodiments of the invention.

DETAILED DESCRIPTION OF THE ILLUSTRATIVE EMBODIMENTS OF THE INVENTION

The present invention provides microneedle devices that may be useful for a variety of purposes. For example, the microneedle devices may be used to deliver or remove fluids from the point at which they are inserted. To accomplish that goal, the microneedle devices include a capillary volume in contact with the base of each of the microneedles.

The microneedle devices of the present invention may be used for a variety of purposes. For example, the microneedle devices may be used to deliver drugs or other pharmacological agents through the skin in a variation on transdermal delivery. Where the microneedle devices are to be used for transdermal drug delivery, the height of the microneedles is preferably sufficient to pass through the stratum corneum and into the epidermis. It is also, however, preferable that the height of the microneedles is not sufficiently large to cause significant pain when inserted at a delivery site.

As used in connection with the present invention, the term "microneedle" (and variations thereof) refers to structures having a height above the surface from which they protrude of about 500 micrometers or less. In some instances, microneedles of the present invention may have a height of about 250 micrometers or less.

Although the illustrative microneedle devices described herein all include multiple microneedles, it will be understood that microneedle devices of the present invention may include only one microneedle on each substrate. Further, although the microneedle devices are all depicted with only one substrate, each device could include multiple substrates, with each substrate including one or more microneedles protruding therefrom.

Figure 1:
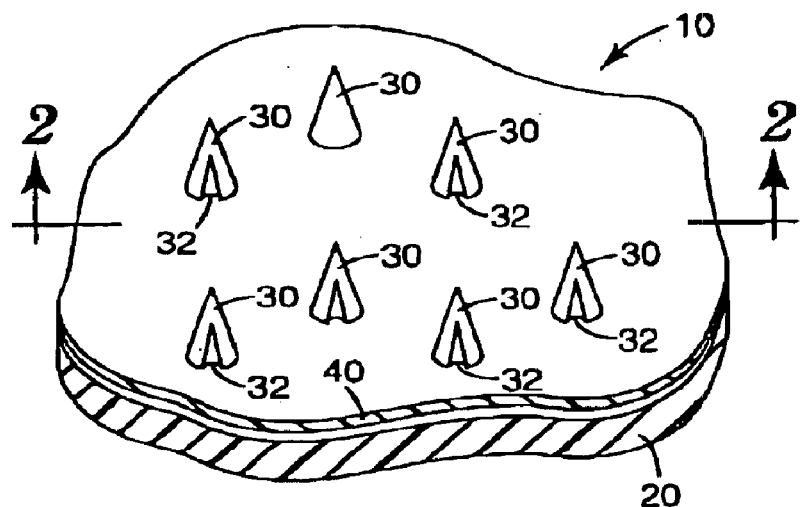
FIG. 1 is a perspective view of one microneedle device according to the present invention.
Figure 2:
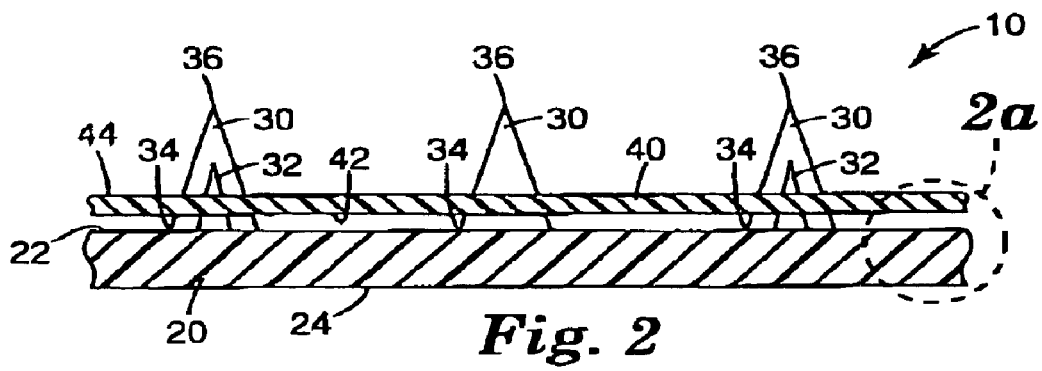
FIG. 2 is a cross-sectional view of the microneedle device of FIG. 1, taken along line 2—2 in FIG. 1.
Figure 2A:
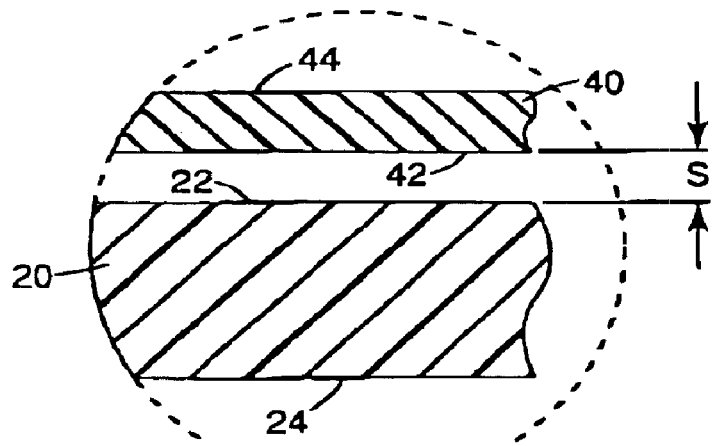
FIG. 2A is an enlarged cross-sectional view of a portion of the microneedle device of FIG. 2 (indicated by boundary 2A in FIG. 2).

Referring now to FIGS. 1, 2 and 2A, a portion of one microneedle device 10 is illustrated with microneedles 30 protruding from a surface 22 of a microneedle substrate 20. The microneedles 30 may be arranged in any desired pattern or distributed over the surface 22 randomly. The microneedles 30 may each include a channel 32 formed in the outer surface of the tapered microneedle.

The microneedles 30 each include a base 34 proximate the substrate surface 22 and a tip 36 distal from the base 34. The general shape of the microneedles 30 is tapered. For example, the microneedles 30 have a larger base 34 at the substrate surface 22 and extend away from the substrate surface 22, tapering towards a tip 36. It may be preferred, e.g., that the shape of the microneedles used in connection with the present invention be generally conical.

Each of the microneedles in the depicted device 10 may also preferably include a channel 32 that extends from the base 34 (or near the base) of the microneedle towards the tip 36 of the microneedle. The channels may typically be formed as a void running along the side of the exterior surface of the microneedle 30. In some embodiments, the channel 32 may extend to the tip 36 of the microneedle 30 and, in other embodiments, the channel 32 may terminate before reaching the tip 36.

The channels 32 formed in microneedles 30 of the present invention can be distinguished from bores or vias formed in other microneedles because they are open along substantially their entire length, e.g., from the base 34 of the microneedle 30 to the terminus of the channel 32. In contrast, bores or vias formed in other microneedles are typically closed fluid pathways that have an opening at the tip of the microneedle structure.

In some embodiments, the bases of the microneedles may be elongated to improve the rigidity and structural integrity of the microneedles. In the microneedles with bases that are elongated along an elongation axis, it may be preferred that the channels extend from one of the opposing ends located along the elongation axis.

These and other variations in channeled microneedles are described in more detail in U.S. patent application Ser. No. 09/947,195, filed on Sep. 5, 2001 and entitled MICRONEEDLE ARRAYS AND METHODS OF MANUFACTURING THE SAME. It may, for example, be preferred that the microneedles 30 include elongated bases as described in the identified application.

Referring to FIGS. 2 and 2A, the microneedle device 10 includes substrate 20 with major surface 22 from which the microneedles 30 protrude. The substrate 20 may also include a substantially flat opposing major surface 24 on the opposite side of the substrate 20.

The microneedle device 10 also includes a cover 40 located over the major surface 22 of substrate 20. The cover 40 includes two major sides 42 and 44, with major side 42 being oriented to face the major surface 22 of the substrate 20. Each of the microneedles 30 preferably pierces through the cover 40, such that the base 34 of each microneedle 30 is located within a volume defined between the major surface 22 of the substrate 20 and the side 42 of the cover 40.

It may be preferred, but not required, that the cover 40 be provided in the form of a liquid impermeable film, more preferably a polymeric film. One example of a suitable polymeric film may be, e.g., a simultaneously biaxially oriented polypropylene film (with a thickness of, e.g., about 10 to about 20 micrometers). Regardless of the material or materials used for the cover, it should be understood that although the cover is depicted as a single-layer homogenous structure, it may be a non-homogeneous structure, e.g., a multi-layer construction, a binder containing one or more fillers, or any other suitable design.

The thickness of the cover may vary based on the height of the microneedles and their intended use, although covers with a thickness less than the height of the microneedles may be preferred. If the cover is too thick, however, it may interfere with penetration of the delivery site by the microneedles. Thicker covers may, however, be used if, for example, they are compressible to allow for penetration of the delivery site by the microneedles when the cover is compressed. In such a situation, a compressible cover with an uncompressed thickness equal to or greater than the height of the microneedles may be acceptable.

The volume thus defined between the substrate surface 22 and the cover 40 is the capillary volume. The spacing or distances s (see FIG. 2A) between the substrate surface 22 and the side 42 of the cover 40 facing the substrate 20 may be controlled by a variety of techniques. In some instances, the distance or spacing that defines the capillary volume will only be loosely controlled, without the assistance of any structures. In other instances, some of which are discussed below, the spacing s may be controlled by standoff structure located within the capillary volume.

The spacing s is selected to provide the desired capillary or wicking action required to transport fluid through the capillary volume, either towards the microneedles 30 or away from the microneedles 30. It is preferred that the distance s be greater than zero at the lower end, in some instances about 10 micrometers or more. At the upper end, it may be preferred that the capillary volume have a distance s that is about 100 micrometers or less, more preferably about 40 micrometers or less.

In addition to control over the spacing s to facilitate fluid transport through the capillary volume, the materials used to form the substrate 20 and/or the cover 40 may also be selected for their hydrophilic properties to facilitate fluid transport through the capillary volume. Alternatively, or in addition to materials, the surfaces within the capillary volume may be structured to enhance fluid transport through the capillary volume.

In another alternative, one or more surfaces within the capillary volume may be provided with a hydrophilic coating to enhance fluid transport. Examples of suitable hydrophilic coatings are provided by coating the desired surface or surfaces using a surfactant solution that includes from about 0.05% to about 0.5%, by weight, branched chain sodium dodecylbenzene sulfonate and from about 0.10% to about 0.6%, by weight, ethoxylated acetylenic diol, in a solvent including a 70/30 mix of isopropyl alcohol and water.

Referring again to FIG. 2A, if the microneedles 30 include channels 32 formed along their exterior surfaces, it may be preferred that the channels 32 be in fluid communication with the capillary volume formed between the substrate 20 and the cover 40. Putting the channels 32 in fluid communication with the capillary volume will typically enhance the transport of fluids through the microneedle device 10.

Although only one type of channel 32 is depicted in FIGS. 1 and 2, it should be understood that any suitable channel structure may be provided in connection with the microneedles of the present invention. Further, the microneedles may be provided without channels if fluid transport along the exterior surface of the microneedles can be provided in the absence of channels. For example, the exterior surfaces of the microneedles may be textured or otherwise treated to improve the ability of fluids to move along the surface of the microneedles. Those treatments may, in some instances, include the hydrophilic coatings described above.

Figure 3:
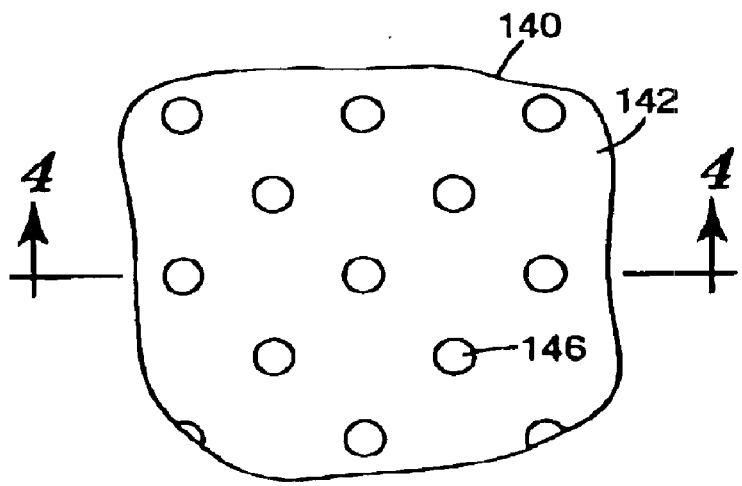
FIG. 3 is a plan view of a portion of one side of a cover including a standoff structure that may be used in connection with the microneedle devices of the present invention.
Figure 4:
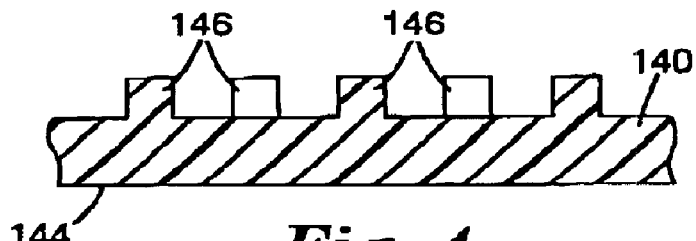
FIG. 4 is a cross-sectional view of the cover of FIG. 3, taken along line 4—4 in FIG. 3.

Turning to FIGS. 3 and 4, the spacing between the substrate and a cover 140 may be controlled by, e.g., standoff structure 146 provided on the cover 140. FIG. 3 depicts one example of a standoff structure that may be useful in connection with the present invention. The standoff structure 146 includes pillars formed such that they protrude from the surface 142 of the cover 140. The pillars may be of substantially the same height as depicted in FIG. 4, or they may be of different heights if so desired. The spacing between the pillars may also vary depending on the specific application of the microneedle device.

Although the depicted standoff structure 146 is in the form of circular cylindrical pillars, it should be understood that the standoff structure may be provided in any suitable shape or combination of shapes, e.g., pyramids, hemispherical protrusions, walls, etc.

It may be preferred that the standoff structure 146 be formed integrally with the cover, e.g., as a structured surface molded or otherwise formed in the cover material. Alternatively, the standoff structure may be provided in the form of separate articles attached to the cover (e.g., loosely bonded fillers, microbeads, cube corner elements, etc.).

Figure 5:
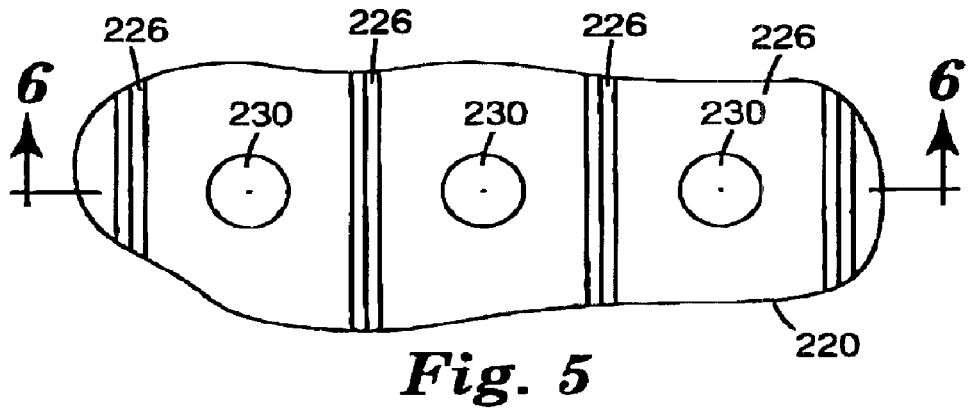
FIG. 5 is a plan view of a portion of microneedle substrate surface including standoff structure that may be used in connection with the microneedle devices of the present invention.
Figure 6:
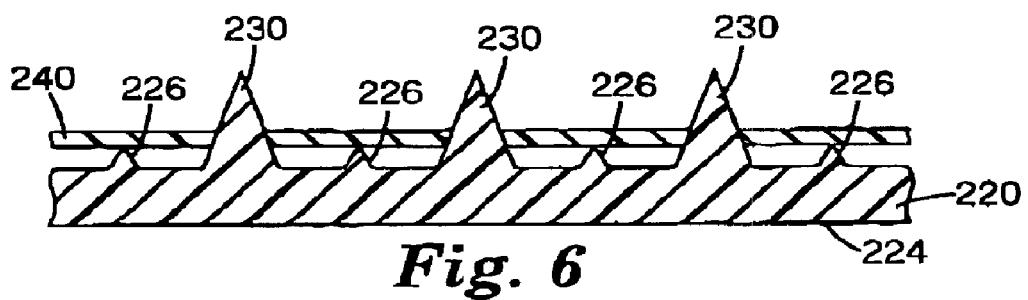
FIG. 6 is a cross-sectional view of the substrate of FIG. 5, taken along line 6—6 in FIG. 5 (with a cover added to illustrate the function of the standoff structure).

FIGS. 5 and 6 depict another variation in standoff structures that may be used in connection with the present invention with a cover 240 present in FIG. 6 to illustrate the function of the standoff structure 226 in spacing the cover 240 from the surface 222. The standoff structure 226 is formed such that it protrudes from the surface 222 of the microneedle substrate 220. The depicted standoff structure 226 is in the form of elongated prisms that may preferably define channels or conduits in which the microneedles 230 are located. In some instances, these elongated standoff structures 226 may provide some directionality to fluid flow through the capillary volume formed between the cover 240 and the substrate 220, with fluid flow being generally controlled along the direction of the elongated standoff structures 226.

It may be preferred that the standoff structure 226 be formed integrally with the substrate 220, e.g., as a structured surface molded or otherwise formed in the substrate 220. Alternatively, the standoff structure may be provided in the form of separate articles attached to the substrate (e.g., loosely-bonded fillers, prisms, microbeads, cube corner elements, etc.).

It should be understood that in some instances the standoff structure may not be attached to any surface within the capillary volume and may, instead, take the form of particulates dispersed within the capillary volume.

Figure 7:
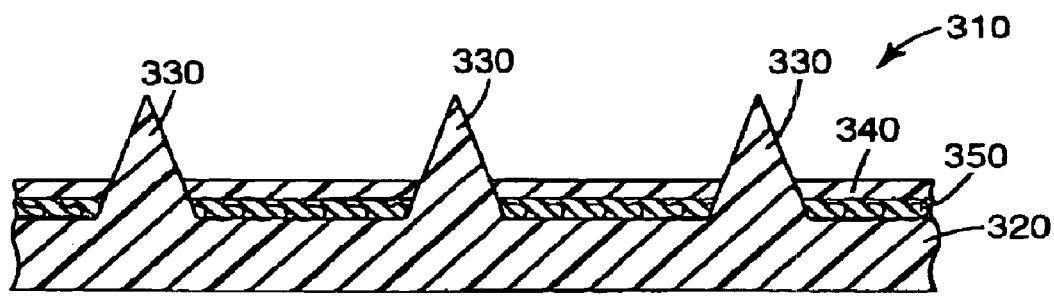
FIG. 7 is a cross-sectional view of a portion of another microneedle device according to the present invention.

FIG. 7 depicts yet another variation in a microneedle device 310 according to the present invention. The device 310 includes a substrate 320 from which microneedles 330 protrude. The microneedles 330 pierce a cover 340 as described above, with a capillary volume being defined between the substrate 320 and the cover 340. In the embodiments described above, the capillary volume is largely open and unobstructed (with the exception of the microneedle bases and any standoff structure located within the capillary volume). In the embodiment depicted in FIG. 7, however, a standoff structure in the form of a porous layer 350 is shown.

The porous layer 350 may preferably be largely coextensive with the capillary volume, such that the open volume of the capillary volume is provided by the pores or interstices within the porous layer 350. Alternatively, the porous layer 350 may be provided in separated, discrete locations across the surface of the substrate 320. The porous layer 350 may take a variety of constructions, provided that the movement or passage of fluid therethrough is provided for. Examples of some suitable materials for the porous layer 350 may include papers, treated papers, polymers, woven fibers, such as fabrics, or non-woven materials. For example, wet laid products such as paper, spun-laced non-woven, spun-bonded non-woven, polyurethane open and closed-celled foams, carded web non-woven, blown microfiber non-woven, woven fabrics selected from the group consisting of cotton, cellulose, rayon, acetate, polyester, nylon, polypropylene, polyethylene, urethane, glass, metal, and blends thereof may, in some instances be used.

In some constructions, the porous layer 350 alone may function as the cover, with no cover layer 340 present. In such a construction, the thickness of the porous layer 350 above the substrate 320 will define the boundaries of the capillary volume. Such a porous cover may, for example, be compressible to allow for additional penetration of the microneedles 330 at a delivery site if so desired.

In those constructions, however, in which a separate cover layer 340 is present in addition to a porous layer 350, it may be preferred that the cover layer 340 be provided in the form of a liquid impermeable film, more preferably a polymeric film as discussed above.

Figure 8:
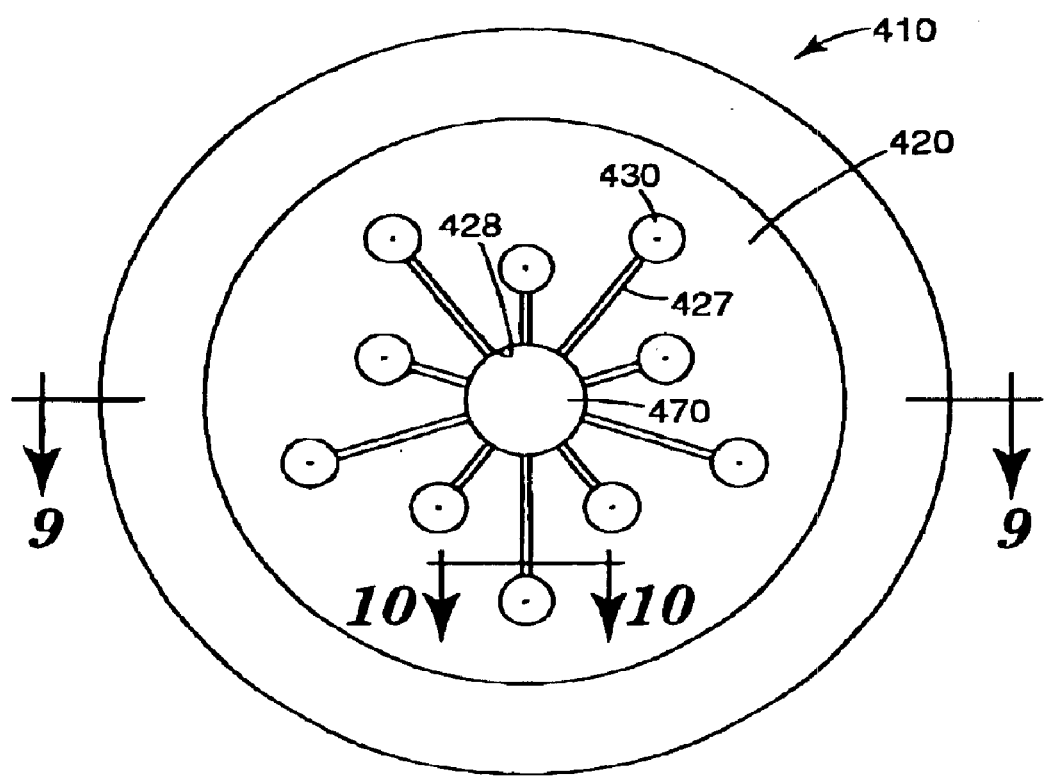
FIG. 8 is a plan view of another microneedle device according to the present invention.
Figure 9:
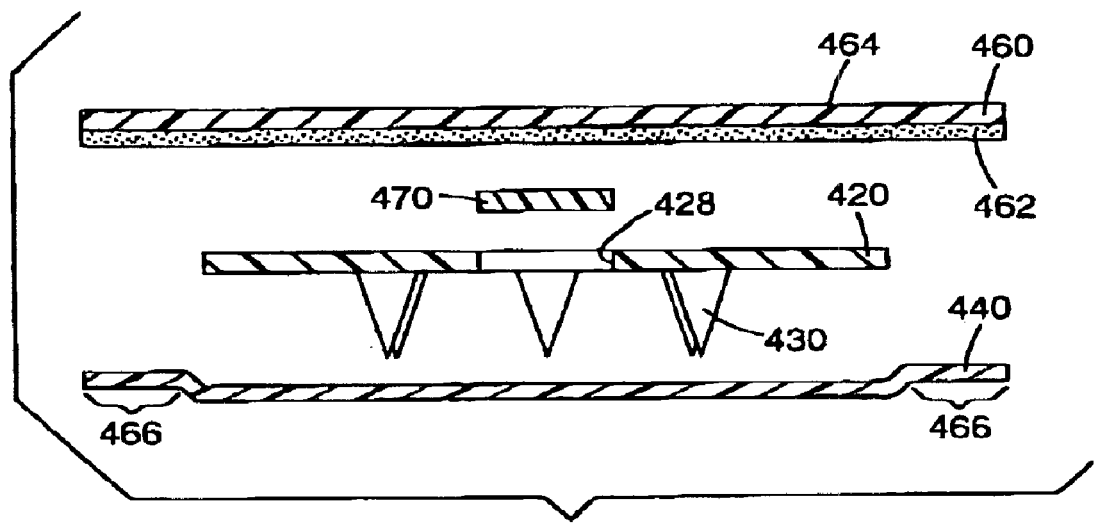
FIG. 9 is an exploded cross-sectional view of the microneedle device of FIG. 8, taken along line 9—9 in FIG. 8.

Turning to FIGS. 8 & 9, another construction for a microneedle device is depicted. The microneedle device 410 includes a substrate 420 from which microneedles 430 protrude. The device 410 also includes a cover 440 through which the microneedles 430 protrude when the device 410 is manufactured. The cover 440 and the substrate 420 define a capillary volume as discussed above.

The device 410 also includes a backing 460 that may be located proximate the opposing surface of the substrate 420 such that the cover 440 faces one major surface of the substrate 420 and the backing 460 faces the opposing major surface of the substrate 420. The backing may preferably include an adhesive 462 such that the backing can be adhered to the substrate 420. The adhesive 462 may preferably be a pressure sensitive adhesive.

If a backing is used in connection with the devices of the present invention, it may be of any suitable construction, including single layer films/foils, multilayer constructions (e.g., poly/foil/poly laminates or multi-layer polymeric film constructions), etc. Examples of some suitable backings may be described in connection with the packaging materials, e.g., U.S. Pat. No. 5,620,095 (Delmore et al.) and U.S. Pat. No. 6,099,682 (Krampe et al.).

The cover 440 and the backing 460 may both preferably extend beyond the periphery of the substrate 420 to form an area 466 in which the cover 440 and the backing 460 are directly opposing each other without the substrate 420 located therebetween. The cover 440 and the backing 460 may preferably be attached to each other about the periphery of the substrate 420 such that the substrate 420 is enclosed within the cover 440 and the backing 460.

The attachment between the cover 440 and the backing 460 may be accomplished by any suitable technique or techniques. For example, the attachment may be accomplished in the depicted embodiment by the adhesive 462 on the backing 460. In other devices, the backing may be attached by, e.g., thermal bonds (e.g., heat seal bonds, welding, etc.), clamps, etc. It may be preferred that the attachment between the cover 440 and the backing 460 be a hermetic seal.

Also depicted in connection with FIGS. 8 & 9 is the inclusion of a sensor element 470 as a part of the microneedle device 410. The sensor element 470 is preferably in fluid communication with the capillary volume defined by the cover 440 and the substrate 420, such that fluids traveling through the capillary volume contact the sensor element 470. Although only one sensor element 470 is depicted in connection with the device 410, it will be understood that devices according to the present invention may include more than one sensor element. Further, the sensor elements may be the same or different.

The sensor element 470 may be used to sense any of a number of properties and/or compositions in the fluids passing through the capillary volume. In one example, the sensor element 470 can be a glucose test element. If, for example, the glucose test element includes glucose oxidaze, the fluid sample passing through the capillary volume may be assessed using electrochemical techniques. In some constructions, the cover, the substrate, or another element (e.g., the backing) may be provided with an electrically conductive circuit pattern to facilitate electrochemical analysis of the fluid sample. Alternatively, the sensor element 470 may be a calorimetric sensor that undergoes an optical change dependent on the properties and/or composition of the fluid passing through the capillary volume. Other alternative sensing techniques will be known to those of skill in the art.

Figure 10:
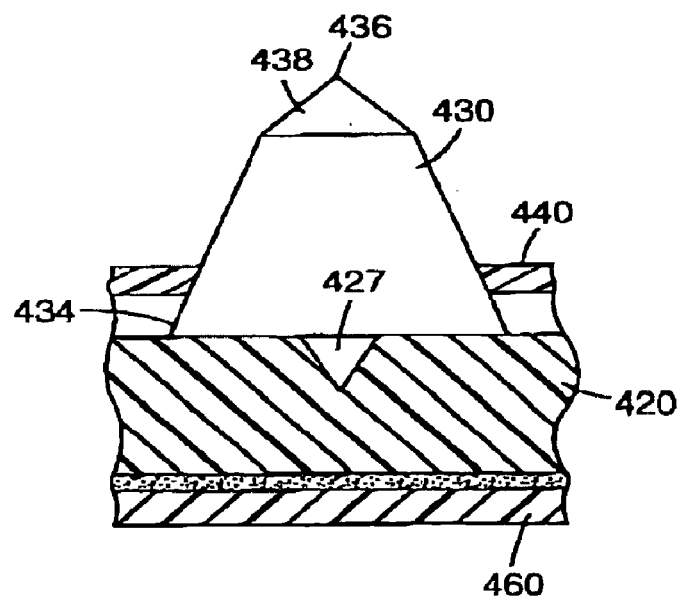
FIG. 10 is an enlarged cross-sectional view of a portion of the microneedle device of FIG. 8, taken along line 10—10 in FIG. 8.

FIG. 10 depicts another feature of the microneedle device 410 in an enlarged cross-sectional view. The additional optional feature is a conduit structure 427 formed into the substrate 420. The conduit structure 427 may be formed as a depression or trench into the substrate 420 as depicted. Alternatively, the conduit structure may be provided as a barrier or barriers provided on the surface of the substrate 420 as discussed in connection with U.S. patent application Ser. No. 09/947,195, filed on Sep. 5, 2001 and entitled MICRONEEDLE ARRAYS AND METHODS OF MANUFACTURING THE SAME.

If the microneedle 430 includes a channel formed therein (as discussed above) it may be preferred that any conduit structure 427 be in fluid communication with the channel. At a minimum, however, it may be preferred that the conduit structure 427 extend to a point proximate the base 434 of the microneedle 430. The conduit structure 427 may be used to deliver fluids to the channels in the microneedles or they may be used to remove fluids from the channels of the microneedles. In some situations, the conduit structure 427 may both deliver and remove fluids from microneedle insertion sites. In some embodiments, the conduit structure may define all or a portion of the capillary volume formed by the substrate 420 and the cover 440. It may be preferred that the conduit structures 427 lead to the void 428 in which the sensor element 470 is located.

Another feature illustrated in FIG. 10 is that the microneedle may have a different shape. Although many microneedles may have a uniform slope or wall angle (with respect to, e.g., a z axis normal to the substrate surface 12), microneedles of the present invention may have different wall angles. For example, FIG. 10 shows microneedle 430 that includes a lower section having steeper wall angles with respect to the substrate 420, and an upper section 438 proximate the tip 436 having shallower wall angles.

In further microneedle shape variations, the microneedles used in connection with the present invention may have generally vertical wall angles, i.e., the microneedles may be in the form of pins, with sidewalls that are largely orthogonal to the surface of the substrate from which they protrude.

Further, although the microneedles and the substrate surfaces of the depicted embodiments are shown with relatively smooth surfaces, the various features of the microneedle devices may have surfaces that are not smooth, e.g., the surfaces may be roughened, structured, etc. to enhance fluid flow over the surface.

Figure 11:
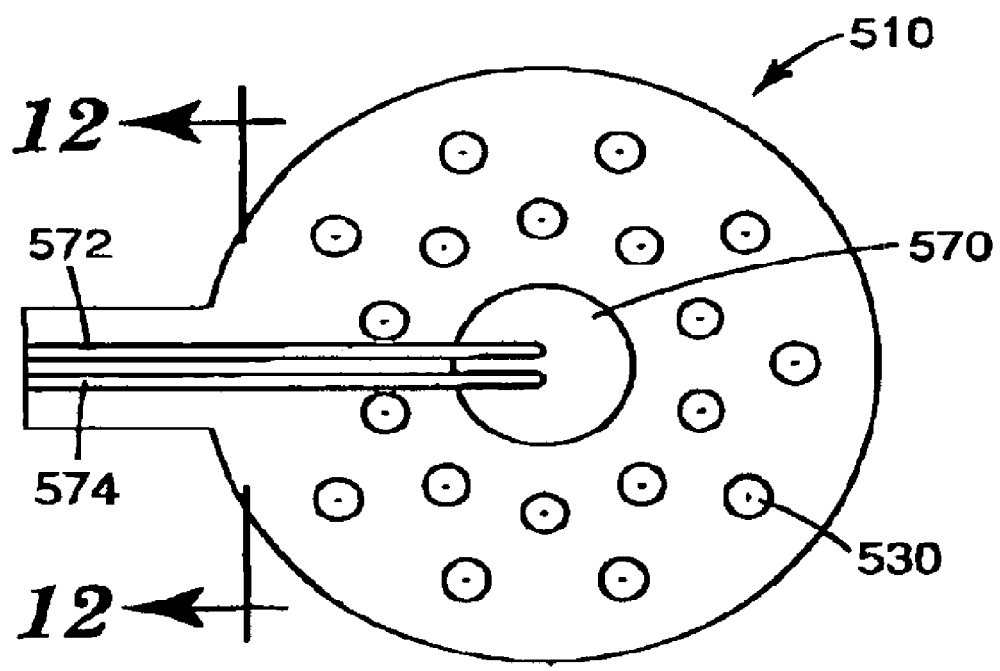
FIG. 11 is a plan view of a microneedle device including a sensor element and electrically conductive circuit pattern.
Figure 12:
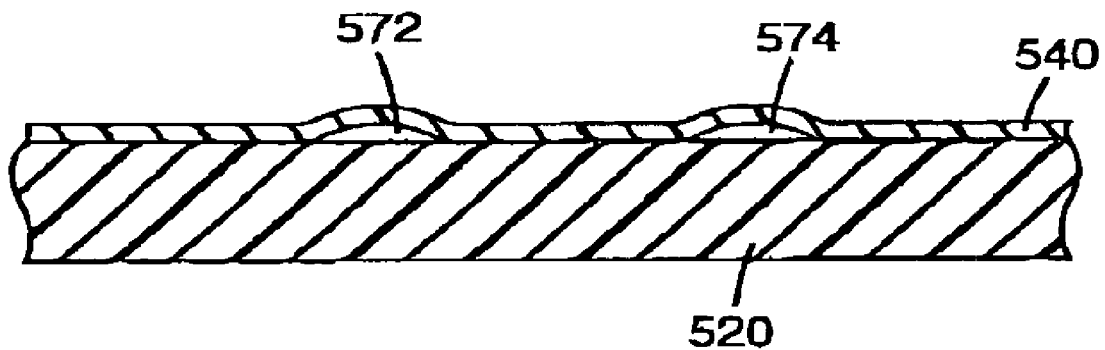
FIG. 12 is a cross-sectional view of the microneedle device of FIG. 11, taken along line 12—12 in FIG. 11.

FIGS. 11 & 12 depict another embodiment of a microneedle device 510 according to the present invention. The device 510 includes a sensor element 570 and a plurality of microneedles 530. The device 510 also includes an electrically conductive pattern in the form of an anode and cathode 572 and 574 respectively. The conductive pattern may be provided in any suitable form, e.g., printed or patterned metallization, conductive polymers, etc. In the depicted embodiment, the conductive pattern is provided on the cover 540, although it will be understood that the conductive pattern may be located at any suitable location or combinations of locations within the device 510 (e.g., on the backing or substrate).

Figure 13:
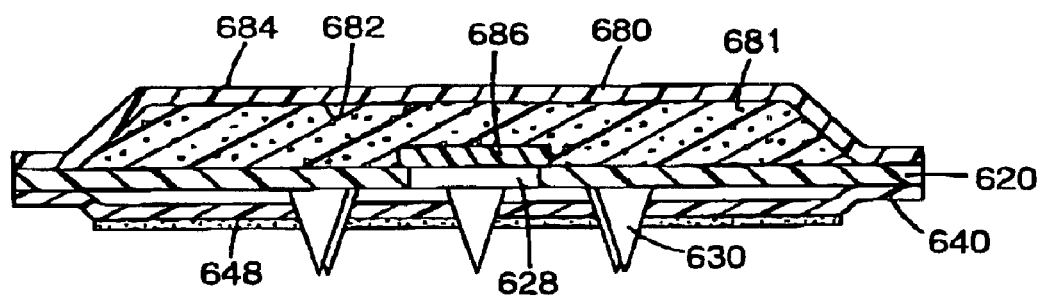
FIG. 13 is a cross-sectional view of another microneedle device according to the present invention.

Another microneedle device 610 according to the present invention is depicted in FIG. 13. The device 610 includes a substrate 620 with microneedles 630 and a cover 640 that form a capillary volume as described above. In addition, the device 610 includes a reservoir volume 681 located on the opposite side of the substrate 620. The reservoir volume 681 may be filled with a fluid including, e.g., a medicament or other pharmacological agent to deliver. The volume 681 is defined by a housing 680 that includes an inner surface 682 facing the substrate 620. The housing 680 (in the depicted embodiment) is attached to the substrate 620 itself on the side opposite the microneedles 630. Alternatively, the housing 680 may be attached to the cover 640 outside of the periphery of the substrate 620. The volume 681 may also include a porous compressible material (e.g., a foam) to assist in holding any fluids or drawing of a vacuum using the device 610 (by compressing the porous material and relying on its tendency to expand, thereby drawing fluids into the volume 681 through void 628).

The substrate 620 preferably includes one or more voids 628 formed therethrough, such that any fluids contained within the reservoir volume 681 can be communicated to the capillary volume formed between the substrate 620 and the cover 640. When the reservoir volume is pressured or compressed (by, e.g., manual pressure), the fluids located within the reservoir volume 681 will preferably tend to flow towards the microneedles 630. If the microneedles 630 are, for example, located within the skin of a patient, the fluids can be delivered to those insertion sites. It may be preferred that the housing 680 be resilient, such that it can substantially recover its shape after compression.

Still another optional feature that may be included in the device 610 is an optional membrane 686 covering the void 628 in the substrate 620. The membrane 686 may prevent fluid communication between the reservoir volume 681 and the capillary volume formed between the substrate 620 and the cover 640. In the absence of the membrane 686 or after the membrane 686 is ruptured or otherwise opened, the reservoir volume 681 is in fluid communication with the capillary volume. Although the membrane 686 is shown as being of a limited size, it may extend to the periphery of the substrate 620 such that it is attached to the housing 680 proximate the periphery of the substrate 620. In such a configuration, the membrane 686 may itself be attached to the substrate 620 by adhesives, thermal bonding, etc. and the reservoir volume 681 may be defined between the membrane 686 and the housing 680.

Opening of the membrane 686 may conveniently be attained by compressing the housing 680 such that the pressure within the reservoir volume causes the membrane 686 to rupture. Other techniques of opening the membrane 686 may also be used. Furthermore, other techniques and structures for sealing the void 628 may be used in place of a membrane 686.

Another optional feature depicted in FIG. 13 is the inclusion of a layer of sealing adhesive 648 on the outer surface of the cover 640. The sealing adhesive 648 may preferably be a pressure sensitive adhesive, that adheres to skin or another delivery site, such that the device 610 is anchored or attached after the microneedles have penetrated at the delivery site. In addition, the sealing adhesive 648 may preferably form a seal about each of the microneedles 630, as well as retain the device 610 in contact with the delivery site. The seal may resist fluid flow and/or allow a vacuum to be drawn at the delivery site. It may be preferred that the sealing adhesive 648 be a skin-compatible adhesive, examples of which are well known. In the depicted device 610, the sealing adhesive 648 may preferably be substantially coextensive with the area occupied by the microneedles 630 such that each of the microneedles 630 is surrounded by the adhesive 648 on the surface of the cover 640.

Figure 14:
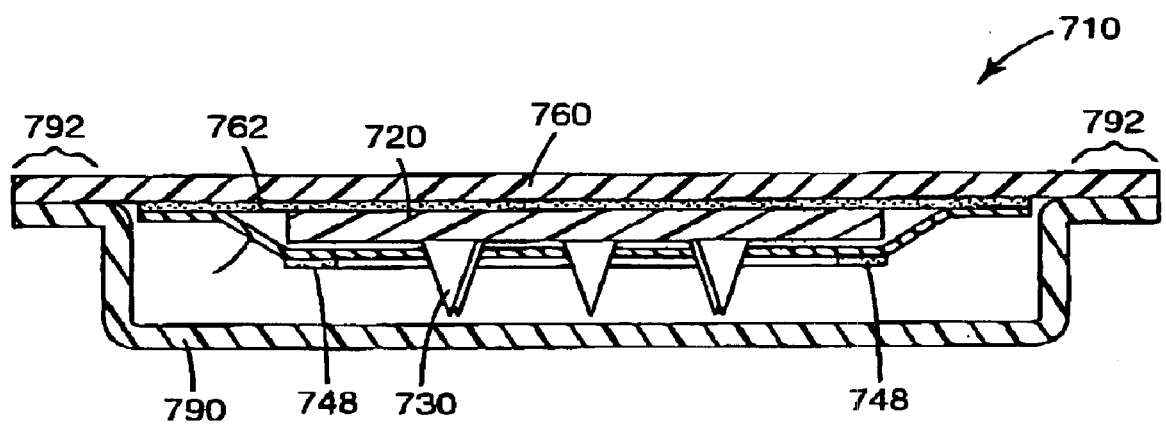
FIG. 14 is a cross-sectional view of another microneedle device according to the present invention.

Another alternative microneedle device is depicted in connection with FIG. 14, and includes a substrate 720, microneedles 730, cover 740 and backing 760. The backing 760 may preferably be attached to the cover 740 about the periphery of the substrate 720 by an adhesive 762. Further, the cover 740 and the substrate 720 form a capillary volume as discussed above.

In the depicted embodiment, the backing 760 extends outside of the substrate 720 and the cover 740 to a peripheral area 792 to which a cap 790 is attached. It may be preferred that the cap 790 and the backing 760 are formed of materials and sealed together by adhesives, thermal bonds, etc. such that the substrate 720 and microneedles 730 are enclosed within a hermetic, moisture-impermeable package used to transport and store the device 710 before use. In such an embodiment, the cap 790 would be removed to expose the microneedles 730 before use. Although the cap 790 is depicted as having a formed shape, it will be understood that it could be formed of flexible, unshaped materials, (e.g., laminates, etc.).

Also seen in FIG. 14, is a ring of sealing adhesive 748 on the outer surface of the cover 740. The ring of sealing adhesive 748 preferably extends about the periphery of the area occupied by the microneedles 730 and provides sealing and/or attachment functions when the microneedles 730 are inserted into a delivery site as discussed above in connection with FIG. 13 and sealing adhesive 648 depicted therein.

Figure 15:
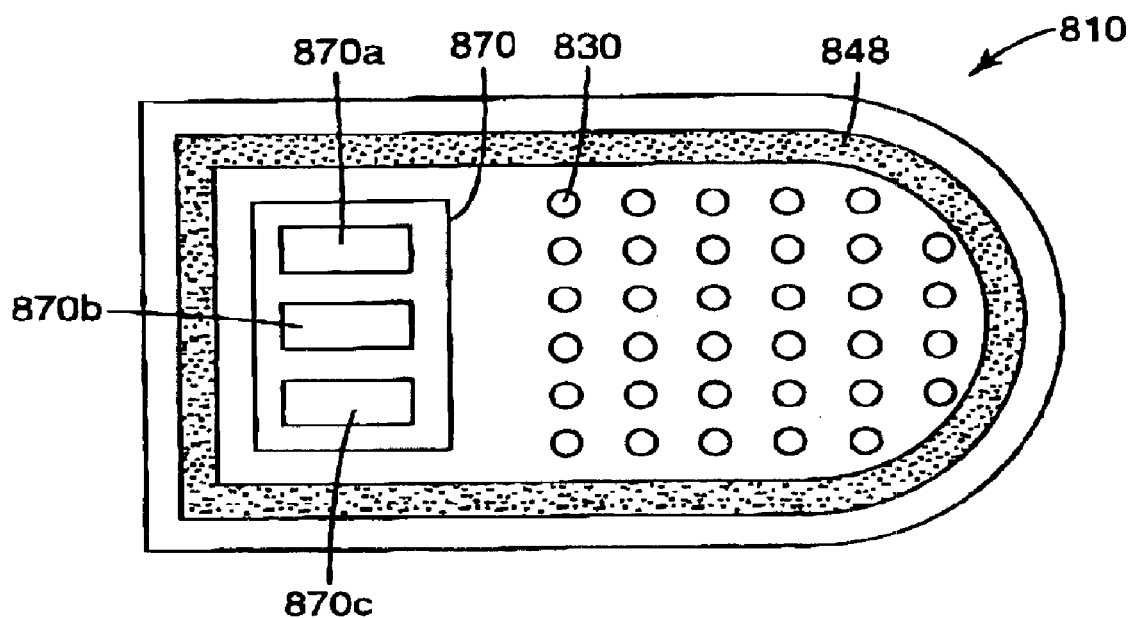
FIG. 15 is a plan view of another microneedle device according to the present invention.

FIG. 15 depicts yet another microneedle device 810 according to the present invention. The device includes microneedles 830 that are preferably segregated in one area of the device 810. A sensor element array 870 is located outside of the area occupied by the microneedles 830 and includes a number of sensor elements 870a, 870b and 870c, all of which may be used to detect the same or different properties or compositions of fluids passing through the capillary volume. In this embodiment, the capillary volume extends over the device such that fluids transmitted into the capillary volume by the microneedles travels across the device 810 into the area occupied by the sensor elements 870. The sensor elements 870 may, for example, be provided in the form of coatings, rather tan separate articles as depicted above.

A ring of sealing adhesive 848 is also depicted in connection with device 810. This ring of sealing adhesive 848 may, for example, be located on a backing that extends beyond the periphery of the substrate on which the microneedles 830 are located (as seen in, e.g., FIG. 14). A cap or liner may then be attached to the adhesive 848 (see, e.g., cap 790 in FIG. 14) to protect it during transport of the device. If a cap is used, it may form a portion of a package in which the device 810 is delivered. Upon removal of the cap or liner, the sealing adhesive 848 is exposed and can be used to attach and/or seal the device 810 to the delivery site.

Figure 16:
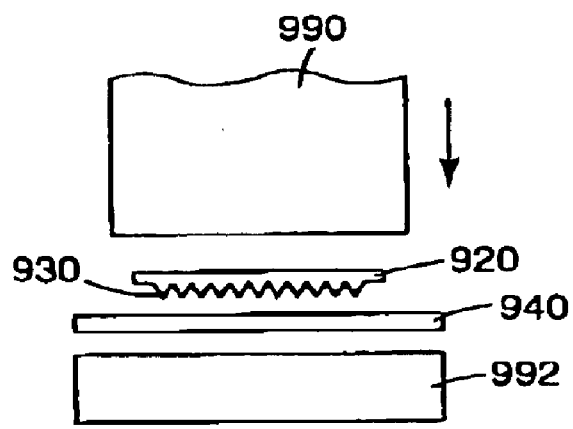
FIG. 16 depicts one portion of one method of manufacturing a microneedle device according to the present invention.

FIG. 16 depicts one method of providing a cover pierced by microneedles in connection with the manufacturing of microneedle devices according to the present invention. The piercing of the cover 940 by the microneedles 930 may be accomplished by any suitable technique or techniques. It may, however, be preferred that piercing of the cover 940 by the microneedles 930 be accomplished by simultaneous delivery of force and ultrasonic energy.

Turning to FIG. 16, the substrate 920 with microneedles 930 may be forced against the cover 940 by an ultrasonic horn 990. It may be preferred that the cover and substrate 920 rest on a resilient material 992 (e.g., silicone rubber having a durometer hardness of approximately 18 on the Shore D scale). As the substrate 920 is forced towards the resilient material 992, ultrasonic energy may assist the microneedles in piercing the cover 940 in a manner that results in the formation of the desired capillary volume as described above.

It is envisioned that other methods of accomplishing piercing of the cover by the microneedles may also be used. For example, it may be desirable to provide heat during the piercing process (alone or in connection with ultrasonic energy). In other instances, it may be sufficient to provide force alone, in some instances an impact force of relatively short duration may be preferred. Furthermore, if ultrasonic energy is used, it may be applied through the cover 940 rather than through the substrate 920 as depicted in FIG. 16.

The microneedles, standoff structure (if any), and conduit structure (if any) may preferably be manufactured integrally with the substrate. In other words, the various features may preferably formed as a one piece, completely integral unit. Alternatively, the microneedles, standoff structures, and/or conduit structures may be provided separately from the substrate.

The microneedle substrates may be manufactured from a variety of materials. Material selection may be based on a variety of factors including the ability of the material to accurately reproduce the desired pattern; the strength and toughness of the material when formed into the microneedles; the compatibility of the material with, for example, human or animal skin; the compatibility of the materials with any fluids to be delivered or removed by the channels formed in the microneedles, etc. For example, it may be preferred that the microneedle arrays of the present invention be manufactured of one or more metals.

Regardless of the materials used for the microneedle arrays of the present invention, it may be preferred that the surfaces of the microneedle array that are likely to come into contact with fluids during use have certain wettability characteristics. It may be preferred that these surfaces are hydrophilic, e.g., exhibit a static contact angle for water of less than 90 degrees (possibly less than about 40 degrees), so that the fluid can be spontaneously wicked via capillary pressure. The hydrophilic nature of the surfaces may be provided by selection of materials used to manufacture the entire microneedle array, surface treatments of the entire array or only those portions likely to come into contact with fluids, coatings on the entire array or only those portions likely to come into contact with fluids, etc.

Microneedles in the microneedle arrays of the present invention can be solid or porous. As used herein, the term "porous" (and variations thereof) means having that the microneedles include pores or voids through at least a portion of the structure, wherein those pores or voids are sufficiently large and interconnected to permit at least fluid passage.

Some suitable processes for forming microneedles of the present invention are described in connection with U.S. patent application Ser. No. 09/947,195, filed on Sep. 5, 2001 and entitled MICRONEEDLE ARRAYS AND METHODS OF MANUFACTURING THE SAME.

The microneedle devices of the invention may be used in a variety of different manners. One manner of using microneedle devices of the present invention is in methods involving the penetration of skin to deliver medicaments or other substances and/or extract blood or tissue. As discussed above, it may be desired that the height of the microneedles in the microneedle devices be sufficient to penetrate the stratum corneum.

All patents, patent applications, and publications cited herein are each incorporated herein by reference in their entirety, as if individually incorporated by reference. Various modifications and alterations of this invention will become apparent to those skilled in the art without departing from the scope of this invention, and it should be understood that this invention is not to be unduly limited to the illustrative embodiments set forth herein.

What is claimed is:

1. A microcedle device comprising:

a substrate comprising a first major surface;

at least one microneedle projecting from the first major surface of the subsrrate, the at least one microneedle comprising a base proximate the first major surface of the substrate and a tip distal from the base;

a cover comprising a first side facing the first major surface of the substrate and a second side facing away from the substrate, wherein the at least one microneedle penetrates through the first side and the second side of the cover;

a capillary volume located between the first major surface of the substrate and the first side of the cover; wherein the capillary volume contacts at least a portion of the base of the at least one microneedle, and a channel formed in an outer surface of the at least one microneedle wherein the channel extends from the base towards the tip of the at least one microneedle.

2. The device according to claim 1, wherein the at least one microneedle comprises a plurality of microneedles.

3. The device according to claim 1, wherein the cover comprises a liquid impermeable polymeric film.

4. A device according to claim 1, further comprising a hydrophilic surface within the capillary volume.

5. The device according to claim 4, wherein the hydrophilic surface comprises a coating.

6. The device according to claim 1, wherein the channel is in fluid communication with the capillary volume.

* * * * *

UNITED STATES PATENT AND TRADEMARK OFFICE
CERTIFICATE OF CORRECTION

PATENT NO. : 6,908,453 B2
APPLICATION NO. : 10/051745
DATED : June 21, 2005
INVENTOR(S) : Patrick R. Fleming It is certified that error appears in the above-identified patent and that said Letters Patent is hereby corrected as shown below:

<u>Column 5:</u>
Line 46, Delete "distances" and insert -- distance --, therefor.

<u>Column 8:</u>
Line 52, Delete "calorimetric" and insert -- colorimetric --, therefor.

<u>Column 12:</u>
Line 62, In Claim 1, delete "microncedle" and insert -- microneedle --, therefor.
Line 65, In Claim 1, delete "subsrrate" and insert -- substrate --, therefor.

<u>Column 14:</u>
Line 5, In Claim 4, delete "A device" and insert -- The device --, therefor.

Signed and Sealed this

Tenth Day of April, 2007

JON W. DUDAS
*Director of the United States Patent and Trademark Office*